(12) United States Patent
Ghosh et al.

(10) Patent No.: US 10,767,314 B2
(45) Date of Patent: Sep. 8, 2020

(54) METHODS TO REDUCE REWINDER BREAKS DURING PAPER PRODUCTION FROM RECYCLED PAPER FURNISH

(71) Applicant: Epygen Labs FZ LLC, Dubai (AE)

(72) Inventors: Debayan Ghosh, Dubai (AE); Punit Bansal, Dubai (AE); Bikas Saha, Dubai (AE); Baljeet Singh, Dubai (AE)

(73) Assignee: Epygen Labs FZ LLC, Dubai (AE)

( * ) Notice: Subject to any disclaimer, the term of this patent is extended or adjusted under 35 U.S.C. 154(b) by 55 days.

(21) Appl. No.: 16/102,519

(22) Filed: Aug. 13, 2018

(65) Prior Publication Data

US 2018/0363249 A1 Dec. 20, 2018

(51) Int. Cl.
| | |
|---|---|
| D21H 21/02 | (2006.01) |
| D21H 17/00 | (2006.01) |
| D21C 9/08 | (2006.01) |
| D21H 23/76 | (2006.01) |
| C12N 9/42 | (2006.01) |
| C12N 9/18 | (2006.01) |
| C12N 9/88 | (2006.01) |
| D21C 5/00 | (2006.01) |
| D21C 9/00 | (2006.01) |

(52) U.S. Cl.
CPC ............. D21H 21/02 (2013.01); C12N 9/18 (2013.01); C12N 9/2437 (2013.01); C12N 9/2445 (2013.01); C12N 9/88 (2013.01); D21C 5/005 (2013.01); D21C 9/008 (2013.01); D21C 9/08 (2013.01); D21C 9/086 (2013.01); D21H 17/005 (2013.01); D21H 23/765 (2013.01); C12Y 110/03002 (2013.01); C12Y 301/01001 (2013.01); C12Y 301/01003 (2013.01); C12Y 302/01004 (2013.01); C12Y 302/01015 (2013.01); C12Y 302/01021 (2013.01); C12Y 402/02002 (2013.01)

(58) Field of Classification Search
USPC ........................................................ 162/199
See application file for complete search history.

(56) References Cited

U.S. PATENT DOCUMENTS

| | | | | |
|---|---|---|---|---|
| 5,620,565 A * | 4/1997 | Lazorisak | ............... | D21C 5/005 162/72 |
| 7,125,471 B2 * | 10/2006 | Hill, Jr. | ............... | D21H 17/74 162/189 |
| 8,048,268 B2 * | 11/2011 | Jiang | ............... | D21C 9/08 162/166 |
| 9,663,899 B2 * | 5/2017 | Gu | ............... | D21D 1/20 |
| 2006/0048908 A1 * | 3/2006 | Wang | ............... | D21C 9/08 162/199 |
| 2008/0169073 A1 * | 7/2008 | Xu | ............... | D21C 9/086 162/199 |
| 2011/0094695 A1 * | 4/2011 | Jiang | ............... | D21C 9/08 162/166 |
| 2012/0211190 A1 * | 8/2012 | Goto | ............... | G01N 5/02 162/198 |
| 2013/0180677 A1 * | 7/2013 | Thomas | ............... | D21B 1/021 162/5 |
| 2015/0053358 A1 * | 2/2015 | Ban | ............... | D21C 5/005 162/5 |
| 2016/0362834 A1 * | 12/2016 | Dale | ............... | D21H 21/36 |
| 2017/0009100 A1 * | 1/2017 | Ling | ............... | C09D 171/02 |
| 2017/0058459 A1 * | 3/2017 | Gu | ............... | D21H 17/455 |

OTHER PUBLICATIONS

Blanco, A. et al., "Overview of Two Major Deposit Problems in Recycling: Slime and Stickies. Part II: Stickies Problems in Recycling," 2002, Prog Pap Recycling 11(2): 26-37.

Brancato, A., "Effect of Progressive Recycling on Cellulose Fiber Surface Properties," 2008, Dissertations & Theses—Gradworks, 26-31.

Doshi, M.R. et al., "Comparison of Microstickies Measurement Methods, Part I: Sample Preparation and Measurement Methods," 2003, Prog Pap Recycling 12(4): 35-42.

\* cited by examiner

*Primary Examiner* — Mark Halpern
(74) *Attorney, Agent, or Firm* — Leydig, Voit & Mayer, Ltd.

(57) ABSTRACT

Methods to reduce sticky and fluff induced rewinder breaks by reducing the adhesive character of adhesive materials, fluff and sticky contaminants in fibers are described. One method involves contacting the fibers with a composition containing at least one of each of a cellulase, a hemicellulase, a β-glucosidase, a lipase, an esterase, a pectinase, a pectate lyase and a laccase for a sufficient time and in a sufficient amount to control the removal or controlling adhesive materials, fluff and sticky contaminants present in the fibers. Preferably, the fibers are recycled fibers originating from a variety of sources such as old corrugated containers, old newsprint, mixed office waste, and the like. Resulting paper products formed from the processed fibers are also described as well as methods to make them.

10 Claims, 9 Drawing Sheets

Figure 1

Stickies breaks at Paper machine dryers & Rewinder

Results-01 (FL 112*: Fluting, 112 GSM)

| SL No. | Time period | Paper Quality | No. of jumbo rolls | No. of paper breaks in dryers | No. of paper joints at rewinder | Percentage of paper breaks in dryers | Percentage of paper joints at rewinder |
|---|---|---|---|---|---|---|---|
| 1 | Blank run 1A | FL 112* | 83 | 7 | 33 | 8.4% | 39.8% |
| 2 | Enzyme "Sample E" | FL 112* | 44 | 0 | 0 | 0.0% | 0.0% |

Results-02 (TL 125*: Testliner, 125 GSM)

| SL No. | Time period | Paper Quality | No. of jumbo rolls | No. of paper breaks in dryers | No. of paper joints at rewinder | Percentage of paper breaks in dryers | Percentage of paper joints at rewinder |
|---|---|---|---|---|---|---|---|
| 1 | Blank run 1B | TL 125* | 121 | 23 | 8 | 19.0% | 6.6% |
| 2 | Enzyme "Sample E" | TL 125* | 89 | 8 | 0 | 9.0% | 0.0% |

Figure 2A

Stickies & Fluff weight collected from Paper machine doctor blades

| SL No. | Time period | Stickies & Fluff weight, (Kgs) | |
| --- | --- | --- | --- |
| | | 1st dryer group | 2nd dryer group |
| 1 | Day 1 (Blank) | 0.730 | 0.130 |
| 2 | Day 2 (Blank) | 0.860 | 0.150 |
| 3 | Day 3 (Blank) | 0.450 | 0.060 |
| 4 | Day 4 (Blank) | 0.450 | 0.060 |
| 5 | Day 5 (Blank) | 0.540 | 0.110 |
| 6 | Day 6 (Blank) | 0.450 | 0.070 |
| Average (Blank) | | 0.580 | 0.097 |
| 7 | Day 7 (Enzyme mix 001) | 0.250 | 0.050 |
| 8 | Day 8 (Enzyme mix 001) | 0.210 | 0.045 |
| Average (Enzyme "Sample E") | | 0.230 | 0.0475 |

| Percentage reduction in stickies & fluff weight | 60.34% | 50.86% |
| --- | --- | --- |

Figure 2B

| SL No. | Parameters | Grade-Fluting, GSM-125 | | | | Percentage joints/breaks | |
|---|---|---|---|---|---|---|---|
| | | Blank | Sample E | | Blank | Sample E |
| 1 | No. of jumbo roll made | 110 | 111 | | | |
| 2 | No. of paper joints at rewinder | 31 | 2 | | 28.18% | 1.80% |
| 3 | No. of paper breaks in paper machine dryers | 8 | 0 | | 7.27% | 0.00% |

Figure 3A

| SL No. | Parameters | Grade- Fluting, GSM-125 | | Percentage joints/breaks | |
|---|---|---|---|---|---|
| | | Blank | Sample A | Blank | Sample A |
| 1 | No. of jumbo roll made | 125 | 121 | | |
| 2 | No. of paper joints at rewinder | 35 | 31 | 28.00% | 25.62% |
| 3 | No. of paper breaks in paper machine dryers | 11 | 9 | 8.80% | 7.44% |

| SL No. | Parameters | Grade- Fluting, GSM-125 | | Percentage joints/breaks | |
|---|---|---|---|---|---|
| | | Blank | Sample B | Blank | Sample B |
| 1 | No. of jumbo roll made | 115 | 118 | | |
| 2 | No. of paper joints at rewinder | 32 | 29 | 27.83% | 24.58% |
| 3 | No. of paper breaks in paper machine dryers | 10 | 9 | 8.70% | 7.63% |

Figure 3B

| Sl No. | Blank | Sample A | Sample B | Sample C | Sample D | Sample E |
|---|---|---|---|---|---|---|
| \*SR at 20 °C (2% OD Fiber) | | | | | | |
| 1 | 12 | 13 | 12 | 13 | 12 | 13 |
| 2 | 12 | 13 | 11 | 11 | 13 | 13 |
| Average | 12 | 13 | 11.5 | 12 | 12.5 | 13 |

Figure 4

| SL No. | Comparison of fiber development | | | | |
|---|---|---|---|---|---|
| | Sample A | Sample B | Sample C | Sample D | Sample E |
| Fiber development | +++ | + | ++ | +++ | ++++ |

Figure 5

| Sl No. | Microscopic pictures observations for Fiber cleanliness | | | | |
|---|---|---|---|---|---|
| | Sample A | Sample B | Sample C | Sample D | Sample E |
| Fiber cleanliness | + | ++++ | +++ | ++ | ++++ |

Figure 6

| SL No. | Comparison of fiber development & fiber cleanliness | | | | |
|---|---|---|---|---|---|
| | Sample A | Sample B | Sample C | Sample D | Sample E |
| Fiber development | +++ | + | ++ | +++ | ++++ |
| Fiber cleanliness | + | ++++ | +++ | ++ | ++++ |

Figure 7

METHODS TO REDUCE REWINDER BREAKS DURING PAPER PRODUCTION FROM RECYCLED PAPER FURNISH

BACKGROUND

Fluff, dust, lint, micro-fibrils and stickies combine together and make a composite, posing biggest technical challenges in using recycled fiber in papermaking. Fluff and stickies cause product quality issues, such as holes and specks in paper as well as paper and rewinder breaks, higher paper rejection or downtime. It is common to have a build-up of black and sticky or gummy deposits on the wire, felts and dryer fabrics. Fluff or lint along with stickies at dryer section has become a serious threat as quality of recycled raw material degrades day by day owing to over recycling.

While producing packaging grade paper from recycled paper furnish e.g. old corrugated containers (OCC), old newsprint (ONP), mixed office waste (MOVV), household waste, often machine runnability and rewinder runnability may be seriously affected due to fluff or lint issue at the dryer section along with stickies. Fluff, dust, lint or fiber and stickies combine together to make a composite, posing one of the biggest challenge in using recycled fiber in papermaking. Fluff and stickies cause product quality issues, such as holes and specks in paper apart from runnabillity issues, even at customers end, leading to higher paper rejection or downtime. It is common to have a build-up of black and sticky or gummy deposits on the wire, felts and dryer fabric. Fluff or lint along with stickies at dryer section has become a serious issue as quality of recycled raw materials is degrading day by day. While doctoring the cylinders became essential to keep the cylinder surface clean but accumulation of fluff and stickies or composite of these two at doctor blades become a serious problem. Frequent machine stoppage due to washing of fabrics and cleaning of doctor blades becomes necessary to maintain good runnabillity at various stages of paper making process and usage e.g at paper machine, winder, converting machine, box making machine etc. All of these problems cause lost production time and mounts a higher cost for the papermaker and converter. It is often difficult to estimate the exact loss due to stickies deposit, since it is often not certain if only the stickies caused the break. This analysis gets more complex as most of the time, stickies sample reveals its composite nature. Typically, a sticky sample could consist of cellulosic materials, extractable organic substances and inorganic components e.g. talc, calcium carbonate, silicate etc.

It is therefore relevant to understand stickies and fluff or lint issues independently and then find an innovative solution for this compound and complex problem called 'Sticky'.

As known to a person skilled in the art, lint is defined as poorly bonded surface material from the surface of the paper sheet. Loosely bonded materials could be fibre, fines, ray cells, fillers, vessels etc.

Lint control strategies can be broadly categorized into three. One commonly used practice being reducing dryer temperatures in the first few sections and ensuring clean smooth dryer surfaces to minimize surface disruptions and hence dusting. Increased press loadings help to reduce dusting. Followed by chemical route being addition of retention aids and other lint control additives to improve retention and thereby control lint or dusting. Internal sizing, Starch addition to the wet end, defoamers and more recently specialized roll release aid chemicals, which contains hydrocarbon materials etc. reduce surface disruption. However, one of the most effective strategies for lint control is to select furnish and develop the fiber in a desired manner with improved fines distribution.

As known to a person skilled in the art, another factor contributing fluff and stickies issue had been water closure in paper mills. This leads to fines build up in the system resulting fluff or lint issue at initial dryers of the drying system. On top of it, stickies issue get compounded as some mills put back recovered fiber/sludge from white water system or mill effluent water treatment plant into pulper or pulp system to achieve high yield.

Generally, the term "stickies" refers to sticky material in the recovered paper but excludes wood extractives. The most common sources of stickies are adhesives used in attaching labels, advertisements, CD's and any other additional material in newspapers and magazines, for binding catalogues, for envelope sealing, stamps, and many more; the other sources of stickies are ink binders and coating binders, i.e. latex. Wax used in carton for packaging is also a significant source of stickies in recycling of old corrugated containers (OCC).

As stated in US Patent 2006/0048908A1, Stickies are classified in two groups. Various adhesives like styrene-butadiene copolymer (SBR), polybutradiene (PBD), polyethylene (PE), and polypropylene (PP); hot melts such as poly-vinyl acetate (PVAc), waxes, resins, vinyl acrylates. Ink residues like resin esters, mineral oils, alkyd resins, styrene-acrylates, and epoxy acrylates; and wet-strength chemicals like urea-formaldehyde considered as synthetic type of stickies.

Natural substances, which contribute to stickies, include fatty acids or esters such as resin acids, wood resins, and, fatty acids, fatty salts, etc. Substances classified as wood extractives may also include, in addition to actual wood resin, fatty acids from deinking aids or resin acids from rosin sizes.

Physically, stickies may be divided into macro, micro and secondary stickies. Macro stickies refer to tacky particles that retain on a laboratory screen of 100 or 150 μm (Blanco et al. 2002; Doshi et al. 2003a; Hamann & Strauss 2002). The size comes from the usual slot size of fine screening. Stickies smaller than 100 or 150 μm, but bigger than 1-5 μm (Doshi et al. 2003a; Hamann & Strauss 2002) are called micro stickies. Dissolved and colloidal stickies smaller than micro stickies are called secondary or potential secondary stickies (Faul 2002; Hamann 2005a). The secondary stickies are thought to become harmful after changes in temperature, pH, or chemical environment (Blanco et al. 2002; Carré et al. 1998; Li & Zhan 2005)

Mills adopt various methods to control stickies and fluff having independent effects or combined effect. As stated in Patent WO 20060294004A1, one of the methods to control stickies is to use expensive wastepaper grades that contain less stickies, however availability of such waste material is scarce and costly. Other methods described for control of stickies are by mechanical means, include cleaning, screening, and dispersion, flotation, washing.

As stated in Patent WO 20060294004A1 the larger or macro stickies are removed by Screening. Centri-cleaners help remove stickies on density differences using centrifugal force. Heavier stickies can be removed by Forward cleaners, whereas lighter particles are removed by reverse cleaners. Flotation helps to remove stickies from back-water or white-water which are intermediate in size stickies. Sludge generated from Flotation Cell contains significant amount of stickies and inorganic substance. Another commonly adopted method to deal with stickies is Dispersion. Pulp is thickened, passed through rotating equipment at high temperature, pressure, and shear, result in breakdowns organic contaminants, including stickies, into smaller pieces.

The fibers that of context for this invention are cellulose fibers and more typically recycled fibers from a variety of paper products or fiber containing products, such as old corrugated containers (OCC), old newsprint (ONP), mixed office waste (MOW), household waste (HW), other recovered paper varieties, or combinations thereof. Recycled fibers are not as strong as virgin fibers due to a loss of hydratability, swelling and fiber flexibility that occurs in the paper forming and drying process.

It was relevant to understand that the main difference between once-dried (secondary) fiber and never-dried (virgin) fiber is that dried fibers are hornified; that is, irreversible fiber bonding within the fiber wall has occurred that resists re-swelling. The drying process has been reported to decrease the specific volume and surface areas of pulp. The dried fibers are difficult to wet because of their glassy crystalline nature compared with the highly amorphous, hydrophilic virgin fiber. In addition, the redistribution of olefinic compounds during drying results in self-sizing. The increased crystallinity of dried fiber also renders the fibers more brittle and difficult to bond leads to dust or lint or fluff generation at pre-dryer section. Hornification is traditionally measured by determining the reduction in the water retention value (WRV) of the pulp after a cycle of drying, although WRV measurement cannot reveal exactly how the fiber has changed. Studies suggest that mechanical pulps resist hornification as evidence that hemicelluloses and possibly lignin inhibit hornification impact. It is indicated, as the Hemicelluloses and lignin on the cellulose fiber surface prevent intrafiber cellulose interaction, by blocking the functional groups on adjacent cellulose surface, the potential for hornification is reduced, and the rewet fiber retains a greater percentage of the available bonding strength it possessed before the initial drying. However, while hemicelluloses can aid in the development of paper strength, lignin inhibits interfiber bond formation, and the inventors brought in a enzyme component in the mix to address the Lignin part (Brancato 2008).

To deal with stickies issues, usual chemical routes include are fixation, detackification etc. Adopting fixation methods, the stickies are attached to the paper sheet by using a suitable polymer. In detackification process, additives like talc, clay, nonionic organic polymers, other inorganic particles, and enzymes are used to convert stickies less tacky in nature.

Other practical approaches being adopted to control fluff and stickies issues are purging white water from selective locations. Avoid using sludge/recovered fiber having lot of contaminations in certain grades of papermaking. Fractionation of pulp and use suitable fraction of the pulp at appropriate layer.

Unfortunately, even with the best of all of these methods, too many of the stickies are still present in the final product to avoid problems.

It is therefore an object of the present invention to reduce rewinder breaks resulting from stickies and their build-up supported by fluff, lints and micro-fibrils.

SUMMARY

Reduction of rewinder breaks by modifying sticky anchoring fiber and removal of this adhesives material, "stickies", from recovered or recycled paper stock was achieved by using a multi enzyme system as defined herein.

A particular inventive combination of these enzymes was found to result in reduction of rewinder breaks by a synergistic action on swelling the fiber, which holds stickies and simultaneously hydrolyzes the microfibers adhering to stickies and further disintegrates ester linkages in the sticky polymer itself, greatly depolymerizing the same as it falls below the critical mass to deposit. A combination of exo cellulase and endo cellulase is used for depolymerizing the glassified crystalline cellulose, anchoring the sticky particle.

A method to reduce rewinder breaks by developing fiber to minimize lint at pre-dryer section and enhancing removal and control of stickies from fibers has been invented. It was surprisingly discovered that rewinder breaks could be reduced due to fiber modification and removal of adhesives materials, "stickies", from recovered or recycled paper stock achieved by using a formulated multienzyme system as defined herein to modify fiber, microfibrils, and the sticky polymer (poly vinyl acetate). Additionally, the pectate lyase breaks down the pectin types of materials holding the sticky particles together, or break the stickies particles free from fines, and lastly the oxidoreductase modify other impurities attached to stickies particles making it more hydrophilic all in a synergistic and orchestrated manner. It is proposed that a suitable combination of these enzymes result in a synergistic action on swelling the fiber, which holds stickies and simultaneously hydrolyzes the microfibers adhering to stickies and further disintegrates ester linkages in the sticky polymer itself, greatly depolymerizing the same as it falls below the critical mass to deposit or build up.

DETAILED DESCRIPTION

In general the terms and phrases used herein have their art-recognized meaning, which can be found by reference to standard texts, journal references and contexts known to those skilled in the art.

A method to develop fiber to minimize lint at pre-dryer section and enhance removal and control of stickies from fibers has been invented. It was surprisingly discovered that fiber modification and removal of adhesives materials, "stickies", from recovered or recycled paper stock could be achieved by using a formulated multienzyme system including, and not limited to hydrolases including exo and endo cellulases, hemicellulases, pectinases and esterases to modify fiber, microfibrils, and the sticky polymer (poly vinyl acetate). Additionally, the pectate lyase breaks down the pectin types of materials holding the sticky particles together, or break the stickies particles free from fines, and lastly the oxidoreductase modify other impurities attached to stickies particles making it more hydrophilic all in a synergistic and orchestrated manner. It is proposed that a suitable combination of these enzymes result in a synergistic action on swelling the fiber, which holds stickies and simultaneously hydrolyzes the microfibers adhering to stickies and further disintegrates ester linkages in the sticky polymer itself, greatly depolymerizing the same as it falls below the critical mass to deposit or build up.

The present invention provides for reduction of rewinder breaks by modifying sticky anchoring fiber and removal of adhesives material, "stickies", from recovered or recycled paper stock. This result was achieved by using a multi enzyme composition including, and not limited to selected hydrolase, lyase and oxidoreductase enzymes. A suitable combination of these enzymes results in a synergistic action on swelling the fiber, which holds stickies and simultaneously hydrolyzes the microfibers adhering to stickies and further disintegrates ester linkages in the sticky polymer itself, greatly depolymerizing the same as it falls below the critical mass to deposit. A combination of exo cellulase and endo cellulase is used for depolymerizing the glassified crystalline cellulose, anchoring the sticky particle.

Figure 1:
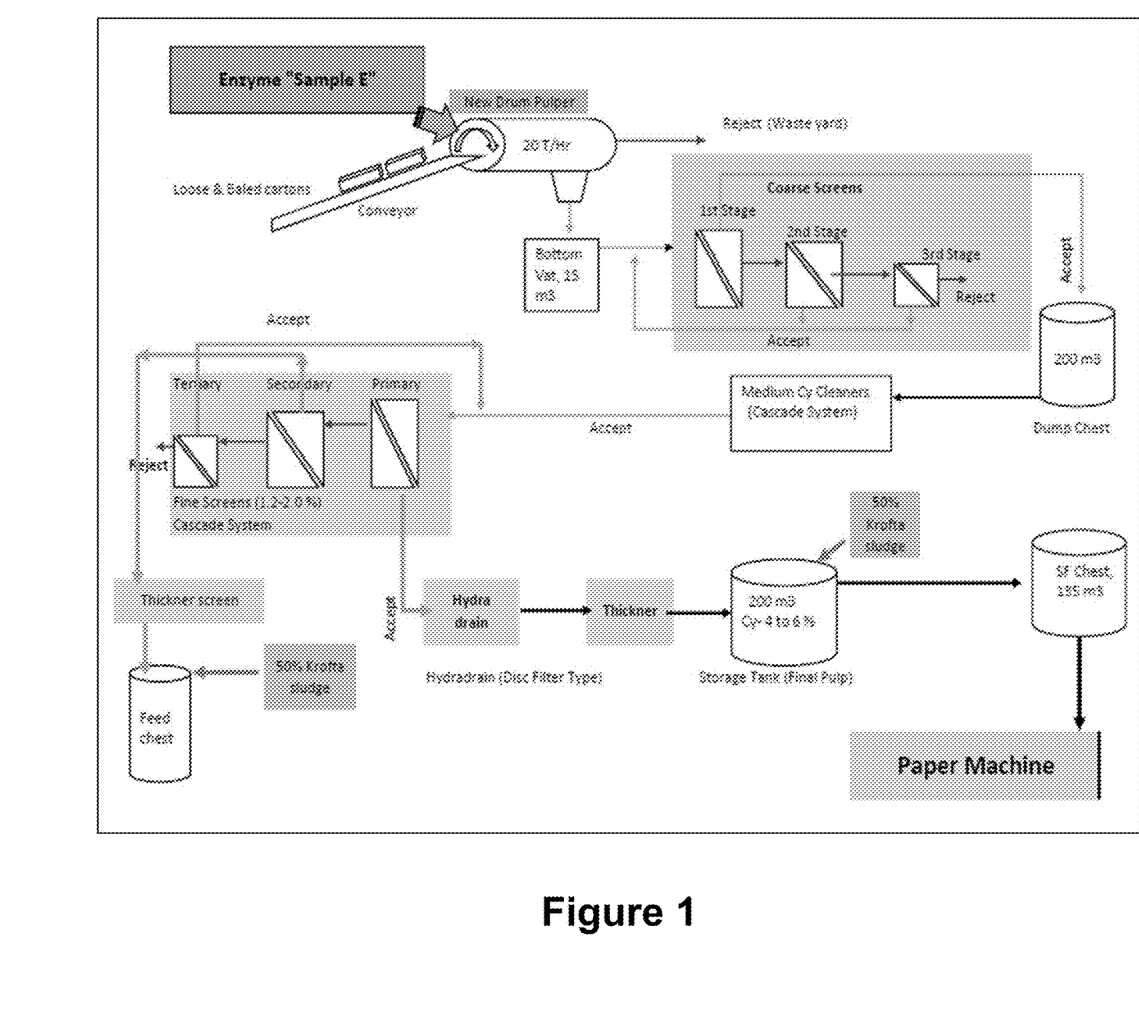
FIG. 1 provides a schematic illustration of a recycled paper pulp processing method.

A typical waste paper processing is shown in FIG. 1. Waste paper processes are known in the art and a typical process is as follows. Initially waste paper is put into a pulper to make pulp slurry, which is screened mechanically known as coarse screening to remove large sized contamination. Subsequently pulp is cleaned by centrifugal mechanism commonly known as centricleaners to remove sand, pins or any contamination, which is heavier than fiber. Thereafter pulp is passed through fine screening system to remove small sized contamination. Typical slot size can be 0.15 mm. Despite application of above methods, substantial amount of stickies are carried forward to paper making process. The proposed reason being stickies are deformable in nature. Their deformability reduces the effectiveness of screening systems by allowing these contaminants to be extruded. In addition to this characteristic, the fact that stickies' specific gravity is so close to that of water and fiber causes them to be accepted by cleaners that are designed to permit water and fiber into the system. Often hot dispersion method is adopted to make any thermolabile sticky melt and washed away. The pulp formed by this method can then be used in any paper machine known in the art with better effect as shown by reduction in stickies breaks in paper machine dryers and rewinder sections, reduction in stickies and fluff weight collected from paper machine doctor blades, reduction in paper breaks in paper machine drying, reduction in number of paper joints at a rewinder, increase in fiber development, among others.

A "rewinder" is a device known in the art used for "converting" large finished rolls to be cut down to size to be used. The parent roll is converted into smaller rolls by the following process. A large master roll of raw product is loaded onto an unwind stand. This is also referred to as a back stand. When the master roll is unwound, it is usually webbed through a slitter/rewinder machine. The word slitter refers to the section of the machine that slits the product into multiple strips. The second part of the slitter/rewinder machine is how the slit product is rewound onto smaller cores to the desired footage or diameter.

It is customary in the paper manufacturing and allied fields to apply an excess of coating composition to a web and to then blade the coating with a flexible "doctor blade." In the blading operation the excess of the coating composition is removed from the web while the remainder of the coating material is troweled or smoothed onto the web surface. The flexible doctor blade may be simply a thin metal blade suitably provided with a ground longitudinally extending blading edge or it may be a small diameter flexible rod supported on an edge of a flexible plate element. Such doctor blade is presented to the web traveling on the backing roll to form an acute angle with a tangent to the backing roll at the line of blade contact.

The multienzyme composition of the present invention could be applied to pulper, dump chest, intermediate tanks, after thickener, washer, water treatment, and storage chests. In the present invention, it was added to the pulper and a good mixing was ensured so that stickies come directly in contact with the enzyme system.

Therefore, the present invention includes a method to reduce sticky and fluff induced rewinder breaks in a paper machine by reducing the adhesive character of the adhesive materials, and/or reducing the fluff and sticky contaminants, in recycled paper fibers for paper production. The present invention also includes methods for reduction in stickies breaks in paper machine dryers and/or rewinder sections, and/or reduction in stickies and fluff weight collected from paper machine doctor blades, and/or reduction in paper breaks in paper machine drying, and/or reduction in number of paper joints at a rewinder, and/or increase in fiber development. The method may include providing recycled paper fibers (e.g., pulp or paper slurry or paper pulp furnish) in aqueous solution; and contacting the recycled paper fibers with a multi-enzyme composition for a sufficient time and in a sufficient amount to reduce the adhesive character of the adhesive materials, fluff and sticky contaminants. In an embodiment, the composition is introduced during the pulping stage.

In an embodiment, the multi-enzyme composition comprises the following enzymes: a cellulase, a hemicellulase, a β-glucosidase, a lipase, an esterase, a pectinase, a pectate lyase and a laccase. The multi-enzyme composition may optionally include one or more of the following enzymes; a cellulase in a concentration of between about 21 and 24% wt/wt of the composition; a hemicellulase in a concentration of between about 21 and 24% wt/wt of the composition; a beta-glucosidase in a concentration of between about 13 and 16% wt/wt of the composition; a lipase in a concentration of between about 14 and 16% wt/wt of the composition, a pectate lyase in a concentration of between about 4 and 7% wt/wt of the composition; an esterase in a concentration of between about 7 and 8% wt/wt of the composition; and a laccase in a concentration of between about 5 and 8% wt/wt of the composition.

In an embodiment, the multi-enzyme composition is capable of hydrolyzing ligno-cellulosic components and enhances the hydration process of recycled fiber. In an embodiment, the multi-enzyme composition is mixed with the pulp slurry in an amount of between 0 ppm and 30 ppm with the pulp slurry weight being calculated based on dry weight of the air-dried fibers in the pulp slurry. In one embodiment, the multi-enzyme composition is added after a step of hot dispersion in the stock preparation process.

The invention also includes a method of making paper or paperboard products. The method may include the steps of forming a pulp slurry comprising fibers obtained from recycled paper or paperboard; treating said slurry with a composition comprising a multi-enzyme composition for a sufficient time and in a sufficient amount to control organic contaminants present in the fiber; and forming the treated slurry into paper or paperboard products.

As noted above, the present invention includes use of hydrolases. A specific formulation was discovered to provide significantly improved results. In the present invention, the composition first includes at least one hydrolase enzyme. A hydrolase enzyme is an enzyme that catalyzes the hydrolytic cleavage of ester or peptide bonds, in which process they use a molecule of water. In hydrolysis reactions, C—O, C—N, and C—S bonds are cleaved by addition of $H_2O$ in the form of $OH^-$ and $H^+$ to the atoms forming the bond. For example, an ester is transformed into an acid and an alcohol molecule; an amide into an amine and acid. Without being bound by theory, it is believed that when the cellobiohydrolase enzymes depolymerize the cellulose chain from its ends, the endoglucanases attack the highly amorphous short fiber or micro-fibrils in the paper web. The micro-fibrils not only entangle the sticky materials, it also adheres to the sticky surface rendering it rough and increasing inter sticky friction and adherence. As the cellulases depolymerize microfibril and pectate lyase attacks the residual lignin of kraft pulp, the sticky particles dislodge from fiber web and the smoothened surface allows them to slide over each other, further reducing building up of critical mass, which would otherwise cause the Sticky mass to be formed.

Enzymes typically include hydrolases, lyases, and oxidoreductases. Individual enzyme or any combinations of them may be applied together with absorbents or adsorbents. Hydrolases include cellulases, β-glucosidases, hemicellulases, pectinases, amylases, proteases, and esterases and other lipases, which may break down poly (vinyl acetate) types of stickies materials. Lyases include pectate lyases, which may break down the pectin types of materials holding the stickies particles together, or break the stickies particles free from fines. Oxidoreductases include laccases, peroxidases, which may modify other impurities attached to stickies particles and make the stickies particles more hydrophilic or free from fibers and/or fines in order to enhance either the stickies removal or make them less troublesome to paper recycling or papermaking processes.

In the composition, there is at least one hydrolase from the following categories. Optionally, there are two, three, four, five, six, seven, eight, or nine of each enzyme from categories (1)-(9) below.

(1) a cellulase (EC 3.2.1.4, cellulase; reaction: endohydrolysis of (1→4)-β-D-glucosidic linkages in cellulose, lichenin and cereal β-D-glucans; other name(s): endo-1,4-β-D-glucanase; β-1,4-glucanase; β-1,4-endoglucan hydrolase; cellulase A; cellulosin AP; endoglucanase D; alkali cellulase; cellulase A 3; celludextrinase; 9.5 cellulase; avicelase; pancellase SS; 1,4-(1,3;1,4)-β-D-glucan 4-glucanohydrolase).

(2) a hemicellulase (EC 3.2.1.4, Hemicellulase; other names, Avicelase; Beta-1,4-endoglucan hydrolase; Beta-1,4-glucanase; Carboxymethyl cellulase; Celludextrinase; Endo-1,4-beta-D-glucanase; Endo-1,4-beta-D-glucanohydrolase; Endo-1,4-beta-glucanase; Endoglucanase; reaction: Endohydrolysis of (1→4)-beta-D-glucosidic linkages in cellulose; lichenin and cereal beta-D-glucan).

(3) an amylase (EC 3.2.1.1; α-amylase; Reaction: Endohydrolysis of (1→4)-α-D-glucosidic linkages in polysaccharides containing three or more (1→4)-α-linked D-glucose units; other name(s): glycogenase; α amylase, α-amylase; endoamylase; Taka-amylase A; 1,4-α-D-glucan glucanohydrolase).

(4) a pectinase (EC 3.2.1.15; polygalacturonase; Random hydrolysis of (1→4)-α-D-galactosiduronic linkages in pectate and other galacturonans. Other name(s): pectin depolymerase; pectinase; endopolygalacturonase; pectolase; pectin hydrolase; pectin polygalacturonase; endo-polygalacturonase; poly-α-1,4-galacturonide glycanohydrolase; endogalacturonase; endo-D-galacturonase; poly(1,4-α-D-galacturonide) glycanohydrolase, β-glucosidases, esterases (enzyme category: EC 3.1, act on ester bonds).

(5) a lipase (EC 3.1.1.3; triacylglycerol lipase; Reaction: triacylglycerol+$H_2O$=diacylglycerol+a carboxylate. Other name(s): lipase; triglyceride lipase; tributyrase; butyrinase; glycerol ester hydrolase; tributyrinase; Tween hydrolase; steapsin; triacetinase; tributyrin esterase; Tweenase; amno N-AP; Takedo 1969-4-9; Meito MY 30; Tweenesterase; GA 56; capalase L; triglyceride hydrolase; triolein hydrolase; tween-hydrolyzing esterase; amano CE; cacordase; triglyceridase; triacylglycerol ester hydrolase; amano P; amano AP; PPL; glycerol-ester hydrolase; GEH; meito Sangyo OF lipase; hepatic lipase; lipazin; post-heparin plasma protamine-resistant lipase; salt-resistant post-heparin lipase; heparin releasable hepatic lipase; amano CES; amano B; tributyrase; triglyceride lipase; liver lipase; hepatic monoacylglycerol acyltransferase.)

(6) a β-glucosidase (EC 3.2.1.21, accepted name: β-glucosidase; Reaction: Hydrolysis of terminal, non-reducing β-D-glucosyl residues with release of β-D-glucose; other name(s): gentiobiase; cellobiase; emulsin; elaterase; aryl-β-glucosidase; β-D-glucosidase; β-glucoside glucohydrolase; arbutinase; amygdalinase; p-nitrophenyl β-glucosidase; primeverosidase; amygdalase; linamarase; salicilinase; β-1,6-glucosidase.

(7) an esterase (EC 3.1.1.1, accepted name carboxylesterase; reaction carboxylic ester plus H2O=an alcohol and a carboxylate; other name(s): ali-esterase; B-esterase; monobutyrase; cocaine esterase; procaine esterase; methylbutyrase; vitamin A esterase; butyryl esterase; carboxyesterase; carboxylate esterase; carboxylic esterase; methylbutyrate esterase; triacetin esterase; carboxyl ester hydrolase; butyrate esterase; methylbutyrase; α-carboxylesterase; propionyl esterase; nonspecific carboxylesterase; esterase D; esterase B; esterase A; serine esterase; carboxylic acid esterase; cocaine esterase.

(8) a lyase. Lyases cleave C—C, C—O, C—N, and C—S bonds by means other than hydrolysis or oxidation. In one embodiment, a lyase is pectate lyase (EC 4.2.2.2; Accepted name: pectate lyase; other names: α-1,4-D-endopolygalacturonic acid lyase; PGA lyase; PPase-N; polygalacturonic acid trans-eliminase; endo-α-1,4-polygalacturonic acid lyase; endogalacturonate transeliminase; endopectin methyltranseliminase; pectate transeliminase; pectic acid lyase; pectic acid transeliminase; pectic lyase; pectin trans-eliminase; polygalacturonate lyase; polygalacturonic acid lyase; polygalacturonic transeliminase. Reaction is eliminative cleavage of (1→4)-α-D-galacturonan to give oligosaccharides with 4-deoxy-α-D-galact-4-enuronosyl groups at their non-reducing ends.

(9) an oxidoreductase: Oxidoreductases catalyze oxidation reduction reactions. At least one substrate becomes oxidized and at least one substrate becomes reduced. In one embodiment, the oxidoreductase is laccase (EC 1.10.3.2;

accepted name: laccase; reaction: 4 benzenediol+O2=4 benzosemiquinone+2H2O; other name(s): urishiol oxidase; urushiol oxidase; p-diphenol oxidase.

In embodiments, the composition comprises at least one enzyme from categories (1), (2), (4), (5), (6), (7), (8), and (9).

In embodiments, the multienzyme composition comprises the following. All percents are given in % wt/wt. For the at least one cellulase, category (1), the amount in the composition can be between 1-60% of the composition, between 5 and 50% of the composition, between 10 and 40% of the composition, between 15 and 30% of the composition, between 20 and 25% of the composition, between about 21 and 24% of the composition, or between about 22 and 23% of the composition. For the at least one hemicellulase, category (2), the amount in the composition can be between 1-60% of the composition, between 5 and 50% of the composition, between 10 and 40% of the composition, between 15 and 30% of the composition, between 20 and 25% of the composition, between about 21 and 24% of the composition, or between about 22 and 23% of the composition. For the at least one pectinase, category (4), the amount in the composition can be between 1-10% of the composition, between 2 and 8% of the composition, between 3 and 6% of the composition, between 3 and 5% of the composition, or between 3 and 4% of the composition. For the at least one lipase, category (5), the amount in the composition can be between 1-40% of the composition, between 4 and 30% of the composition, between 8 and 25% of the composition, between 10 and 20% of the composition, between 12 and 18% of the composition, or between about 14 and 16% of the composition. For the at least one beta-glucosidase, category (6), the amount in the composition can be between 5-25% of the composition, between 8 and 20% of the composition, between 10 and 18% of the composition, between 12 and 17% of the composition, between 13 and 16% of the composition, or between about 14 and 15% of the composition. For the at least one esterase, category (7), the amount in the composition can be between 1-25% of the composition, between 2 and 20% of the composition, between 3 and 15% of the composition, between 4 and 10% of the composition, between 5 and 9% of the composition, between 7 and 8% of the composition, or about 7% of the composition. For the at least one pectate lyase, category (8), the amount in the composition can be between 1-10% of the composition, between 2 and 9% of the composition, between 3 and 8% of the composition, between 4 and 7% of the composition, between 5 and 6% of the composition, or about 6% of the composition. For the at least one laccase, category (9), the amount in the composition can be between 1-15% of the composition, between 2 and 12% of the composition, between 3 and 10% of the composition, between 4 and 9% of the composition, between 5 and 8% of the composition, or about 7% of the composition.

Amounts of each type of enzyme include between about 21 and 24%, or 23%, of the composition of a cellulase; between about 21 and 24%, or 23%, of the composition of a hemicellulase; between about 13 and 16% of the composition, or about 15%, of a beta-glucosidase; between about 14 and 16% of the composition, or about 4% of a lipase, between about 4 and 7%, or about 6%, of the composition of a pectate lyase; between about 7 and 8% of the composition, or about 7% of the composition of an esterase; between about 5 and 8% of the composition, or about 7% of the composition of a laccase.

Additional enzymes may be added to the compositions in amounts of between 1-50%.

The dosage of the enzyme composition may be from 0.0005% to 0.50% w/w based on air dried fibers, preferably from 0.01% to 0.10% based on air dried fibers.

In an embodiment, the multi-enzyme composition is typically added into a pulper, which is used to mix the enzymes thoroughly through the pulp and therefore the reaction can proceed during the time in the pulper and the time in the dump chest. Typical pulping cycles may take up to 60 minutes and mixing time in the subsequent dump chest may be up to 240 minutes. These enzymes may be applied individually or in any combinations and the treatment time be from 1 minute to 16 hours, preferably 10 minutes to 4 hours and most preferably 30 minutes to 60 minutes. The enzymatic treatment pH may be in a range of between 3.5 to 12.0, and preferably between 4.5 and 9.5. The temperature of enzymatic treatment may be in a range of between 35° C. and 90° C., and preferably between 40 to 75° C. The dosage of enzymes may be from 0.0005% to 0.50% based on air dried fibers, more preferably from 0.0025% to 0.25%, and most preferably from 0.05% to 0.15% based on air dried fibers.

Enzymes can also be introduced prior to the pulping stage, typically by spraying or other means, onto the paper containing product which is going to be introduced into the pulper. Also, or alternatively, the enzymes can be present or introduced into the pulper during the pulping stage which can be by any conventional pulping technique such as mechanical pulping or chemical pulping for virgin fibers and batch, semi-batch or continuous pulpers for recycled fiber treatments, or combinations thereof. The enzymes can be introduced or brought into contact at any stock storage chest, other holding tank, or prior to the flotation deinking stage. In one embodiment, the enzymes are introduced after the flotation stage and prior to a washing stage. In another embodiment enzymes are applied prior to fine screens, and in another embodiment enzymes are applied before the paper machine. The composition can also be administered into the paper machine white water or in the makeup water in the deinking plant. Alternatively, the enzymes can be applied in the water treatment loops of virgin or recycling mills to treat stickies in the water filtrates.

The amount of reduction of sticky and fluff induced rewinder breaks in a paper machine (by reducing the adhesive character of the adhesive materials), and/or reduction the fluff and sticky contaminants, in recycled paper fibers for paper production, can be as follows. The reduction can include wherein the breaks are 50% of the control (without enzyme added), 40% of the control (without enzyme added), 30% of the control (without enzyme added), 20% of the control (without enzyme added), 10% of the control (without enzyme added), or 5% of the control (without enzyme added). The present invention also includes methods for reduction in stickies and fluff weight collected from paper machine doctor blades. The reduction can include wherein the percentage reduction in stickies and fluff collected from doctor blades are 90% of the control (without enzyme added), 80% of the control (without enzyme added), 70% of the control (without enzyme added), 65% of the control (without enzyme added), 60% of the control (without enzyme added), or 55% of the control (without enzyme added). The reduction can include reduction in paper breaks in paper machine drying. The reduction can include wherein the breaks are 50% of the control (without enzyme added), 40% of the control (without enzyme added), 30% of the control (without enzyme added), 20% of the control (without enzyme added), 10% of the control (without enzyme added), or 5% of the control (without enzyme added). The reduction can include the reduction in number of paper joints at a rewinder. The reduction can include wherein the paper joints are 50% of the control (without enzyme added), 40% of the control (without enzyme added), 30% of the control (without enzyme added), 20% of the control (without enzyme added), 10% of the control (without enzyme added), or 5% of the control (without enzyme added).

In the examples (Example 1), the multienzyme is added into the pulper, which is used to mix the enzymes thoroughly through the pulp and utilize the time in the pulper and the time in the dump chest for the reaction of the enzymes. Pulping cycles were given 20 minutes and mixing time in the subsequent dump chest was allowed up to 60 minutes. The treatment time was from 15 minute to 15 hours, preferably 30 minutes to 90 minutes. The enzymatic treatment pH was set in a range of between 3.5 to 12.0, and preferably between 4.5 and 9.5. The temperature of enzymatic treatment was set be in a range of between 35° C. and 90° C., and preferably between 40 to 75° C. The dosage of enzymes may be from 0.0005% to 0.50% based on air dried fibers, preferably from 0.01% to 0.1% based on air dried fibers.

The invention may be further understood by the following non-limiting examples.

EXAMPLES

Example 1

The fiber development and fiber cleanliness was studied using the following procedure. Lab study procedure. The equipment and apparatus used were 500 ml beakers, 1000 ml autoclave glass bottles, spatulas, hot air oven, weighing scale, microscope, Schopper Riegler (° SR) tester, pulp disintegrator, and Centigrade thermometer (° C.). The pulp sample was pPrepared using Old Corrugated Container (OCC) furnish and finely distributed stickies material (stickies material was collected from a paper mill and used after grinding and then heating up to 75-80° C. for 30 minutes).

Step 1. Paper slushing. The procedure for OCC paper slushing was as follows: the OCC paper furnish was torn into 2-3 cm² pieces and mixed properly. Then, the pre-determined amount of oven dry OCC paper was transferred to the pulp disintegrator. Then, a pre-determined amount of finely grinded stickies material (5% of oven dry OCC paper) and fresh water was added to the dry OCC to make 4% consistency of pulp slurry. The mixture was thoroughly mixed and slushed up to 3000 revolutions in the pulp disintegrator.

Step 2. For enzyme treatment: A pre-determined amount of pulp slurry was placed in 1000 ml autoclave glass bottle and kept in hot air oven to raise its temperature to 50° C. After getting pulp temperature to 50° C., the sample of Enzyme (250 gram/Ton of oven dry paper) was added and pulp slurry was incubated for 60 min in oven. Oven temperature were kept constant to maintain pulp temperature at 50° C. and pulp bottles were shaken after 10 minutes. Pulp slurry was taken out for (i) Fiber development (ii) Fiber Cleanliness testing after 60 minutes of incubation. Enzyme samples A, B, C, D, and E with enzyme amounts as noted in the below Table 1 were used in the experiments.

TABLE 1

| Description | Cellulase | Hemicellulase | beta-glucosidase | Pectinase | Pectate lyase | Esterase | Lipase | Laccase |
|---|---|---|---|---|---|---|---|---|
| A | 35% | 28% | 17% | 10% | 10% | | | |
| B | | | | | | 48% | 38% | 14% |
| C | 14% | 7% | 7% | 7% | 4% | 29% | 21% | 11% |
| D | 31% | 24% | 19% | 8% | 8% | 8% | 1% | 1% |
| E | 23% | 23% | 15% | 4% | 6% | 7% | 15% | 7% |

The Following conditions were maintained during step 1 and 2. See Table 2.

TABLE 2

| SL No. | Pulp conditions | Blank | With Enzyme |
|---|---|---|---|
| 1 | pH | (6.5-7.5) | 6.5-7.5 |
| 2 | Temp. | 50° C. | 50° C. |
| 3 | Retention/incubation time | 60 min | 60 min |
| 4 | Pulp slurry consistency | 4% | 4% |
| 5 | Enzyme dose | 0.0 gram/Ton of OD pulp | 250 gram/Ton of OD pulp |

OD pulp: Oven dry pulp

Step: 3. Fiber development testing:

Recorded ° SR testing data and microscopic pictures for fibers swelling. For Degree Schopper-Riegler (° SR) testing, TAPPI* standard procedure was followed. Fibers were also evaluated by microscopy. TAPPI*=Technical Association of the Pulp and Paper Industry Step: 4 Fiber cleanliness testing: Prepared 0.1% pulp slurry. Placed a drop of 0.1% pulp slurry into the microscopic slide. Fiber cleanliness has been examined under microscope by comparing the blank and enzyme treated pulp samples. Fiber cleanliness score of the treated samples has been evaluated by using the microscopic pictures.

Results can be seen in FIGS. 2-7.

Example 2

A typical waste paper processing is shown in FIG. 1. Initially waste paper is put into a pulper to make pulp slurry, which is screened mechanically known as coarse screening to remove large sized contamination. Subsequently pulp is cleaned by centrifugal mechanism commonly known as centricleaners to remove sand, pins or any contamination, which is heavier than fiber. Thereafter pulp is passed through fine screening system to remove small sized contamination. Typical slot size can be 0.15 mm. Despite application of above methods, substantial amount of stickies are carried forward to paper making process. The proposed reason being stickies are deformable in nature. Their deformability reduces the effectiveness of screening systems by allowing these contaminants to be extruded. In addition to this characteristic, the fact that stickies' specific gravity is so close to that of water and fiber causes them to be accepted by cleaners that are designed to permit water and fiber into the system. Often hot dispersion method is adopted to make any thermolabile sticky melt and washed away.

Figure 2A:
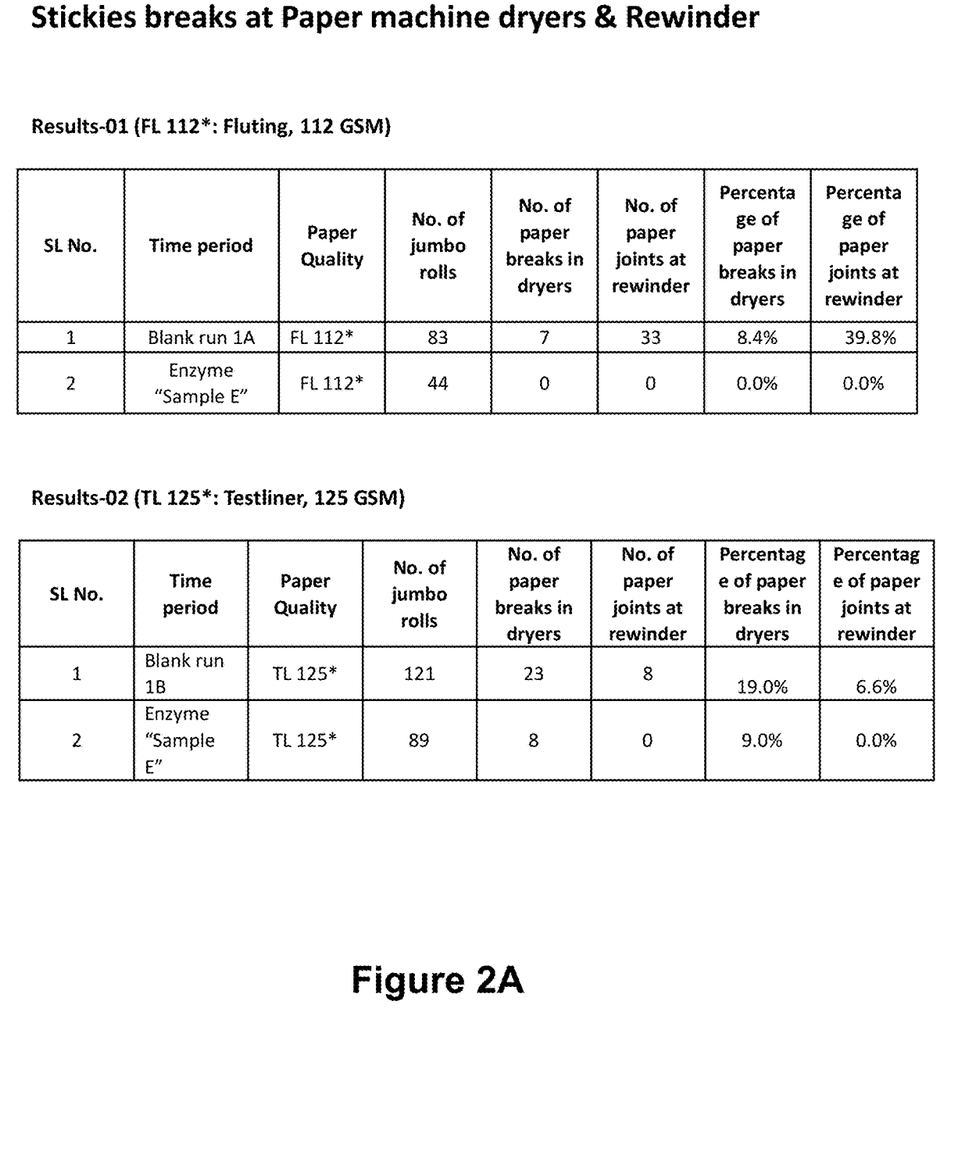
FIG. 2A provides a table showing results of Enzyme formulation "E" on breaks occurring in paper on the paper machine dryer and rewinder, caused by stickies.
Figure 2B:
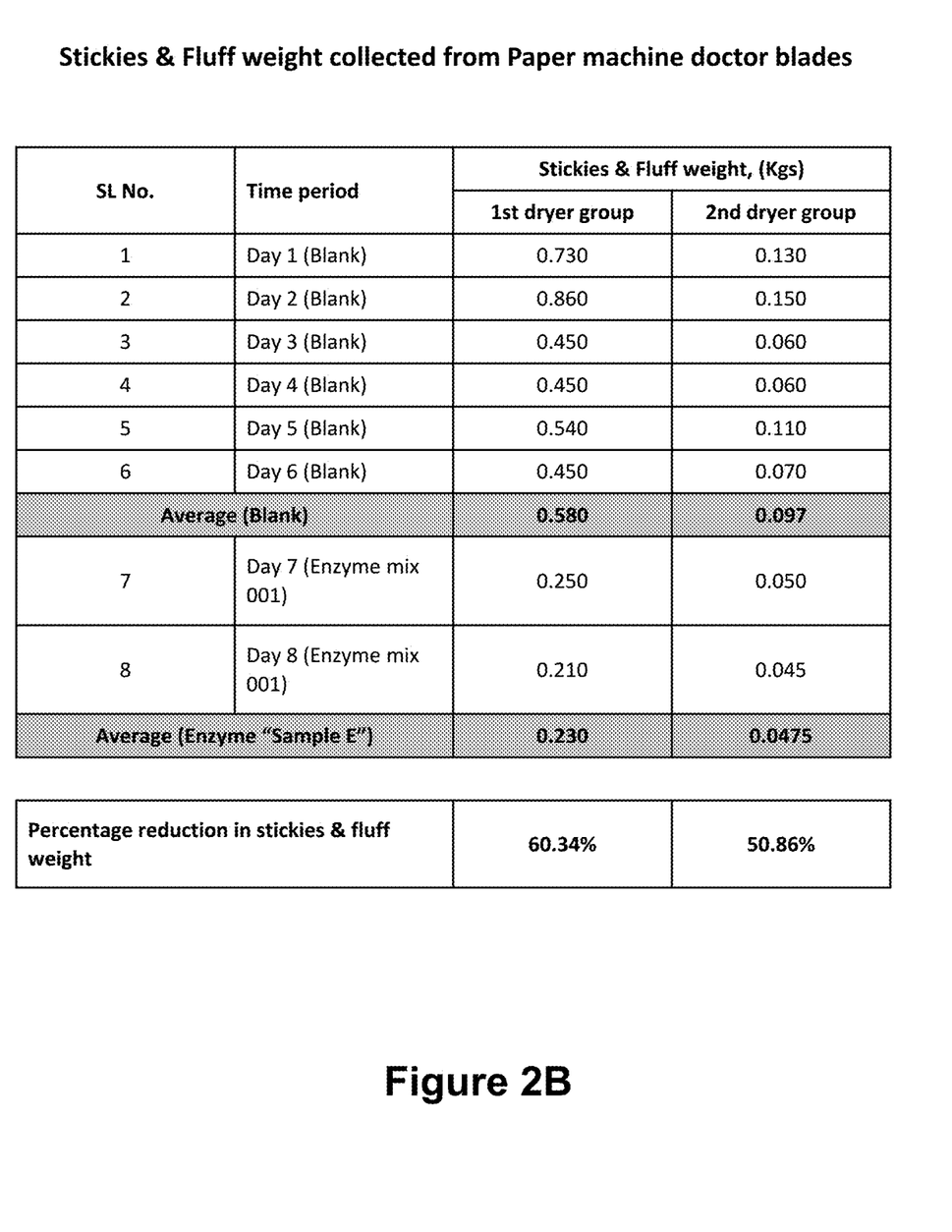
FIG. 2B provides a table showing stickies and fluff weight collected from paper machine doctor blades using Enzyme formulation "E".

Results showing improvements for paper making process for pulp treated with "Sample E" in FIG. 2A-2B.

Paper Machine Details: Machine capacity: 12000 Ton/Month; Grade: Fluting and Test liner; Furnish mix: Mixed OCC; Machine type: Fourdrinier; Speed: 600 m/min; Size press type: Metering size press; Mechanical refiner: No; Hot disperser: Yes.

The multienzyme "E" is added into the pulper, which is used to mix the enzymes thoroughly through the pulp and utilize the time in the pulper and the time in the dump chest for the reaction of the enzymes. Pulping cycles were given 20 minutes and mixing time in the subsequent dump chest was allowed up to 60 minutes. The treatment time was from 15 minute to 15 hours, preferably 30 minutes to 90 minutes. The enzymatic treatment pH was set in a range of between 3.5 to 12.0, and preferably between 4.5 and 9.5. The temperature of enzymatic treatment was set be in a range of between 35° C. and 90° C., and preferably between 40 to 75° C. The dosage of enzymes may be from 0.0005% to 0.50% based on air dried fibers, preferably from 0.05% to 0.15% based on air dried fibers.

Figure 3A:
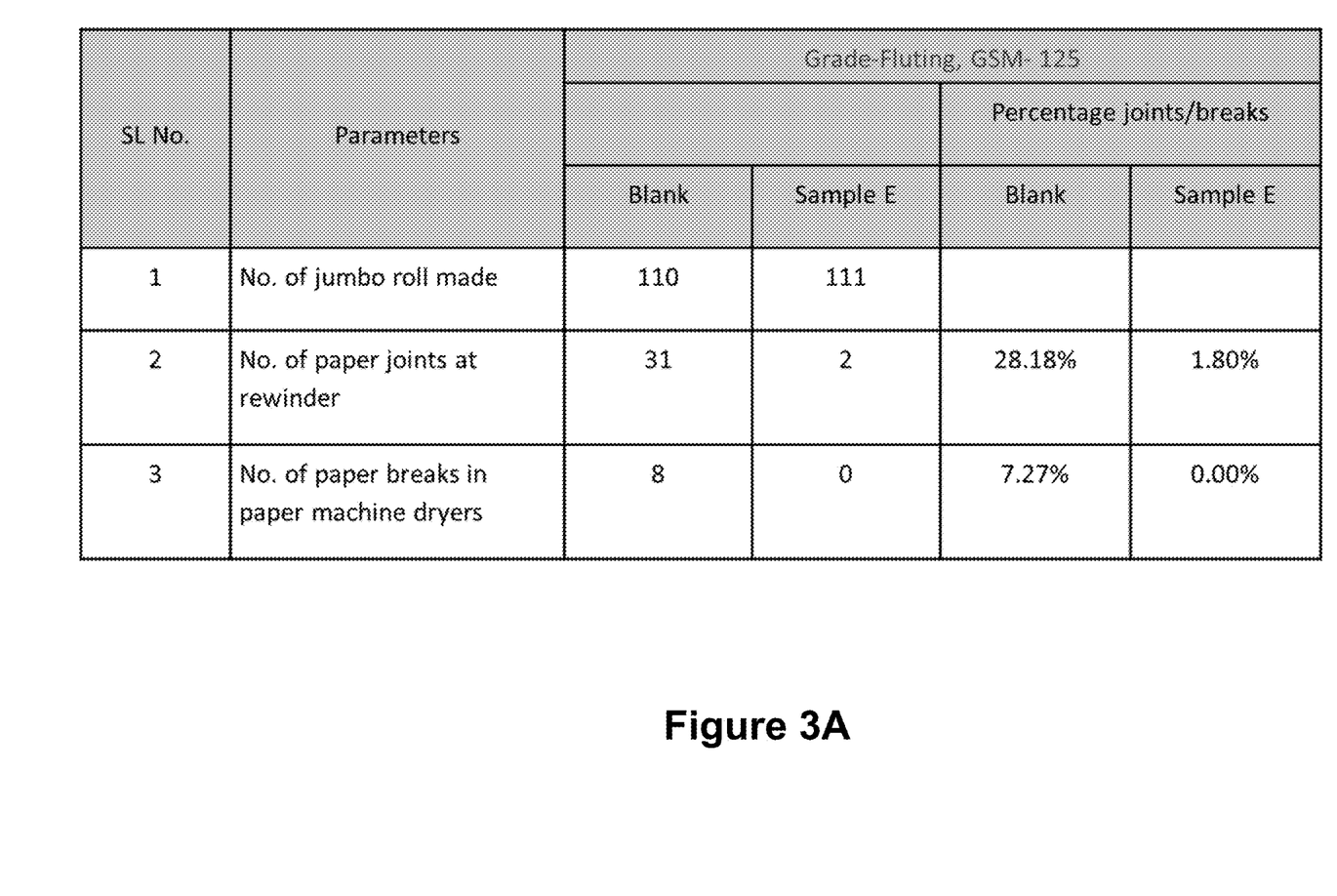
FIG. 3A shows plant trial data for Enzyme formulation "E," showing that when compared to Samples A and B (FIG. 3B), the Sample E shows substantial reduction of Rewinder Breaks and Paper Breaks in machine, proving the invention.
Figure 3B:
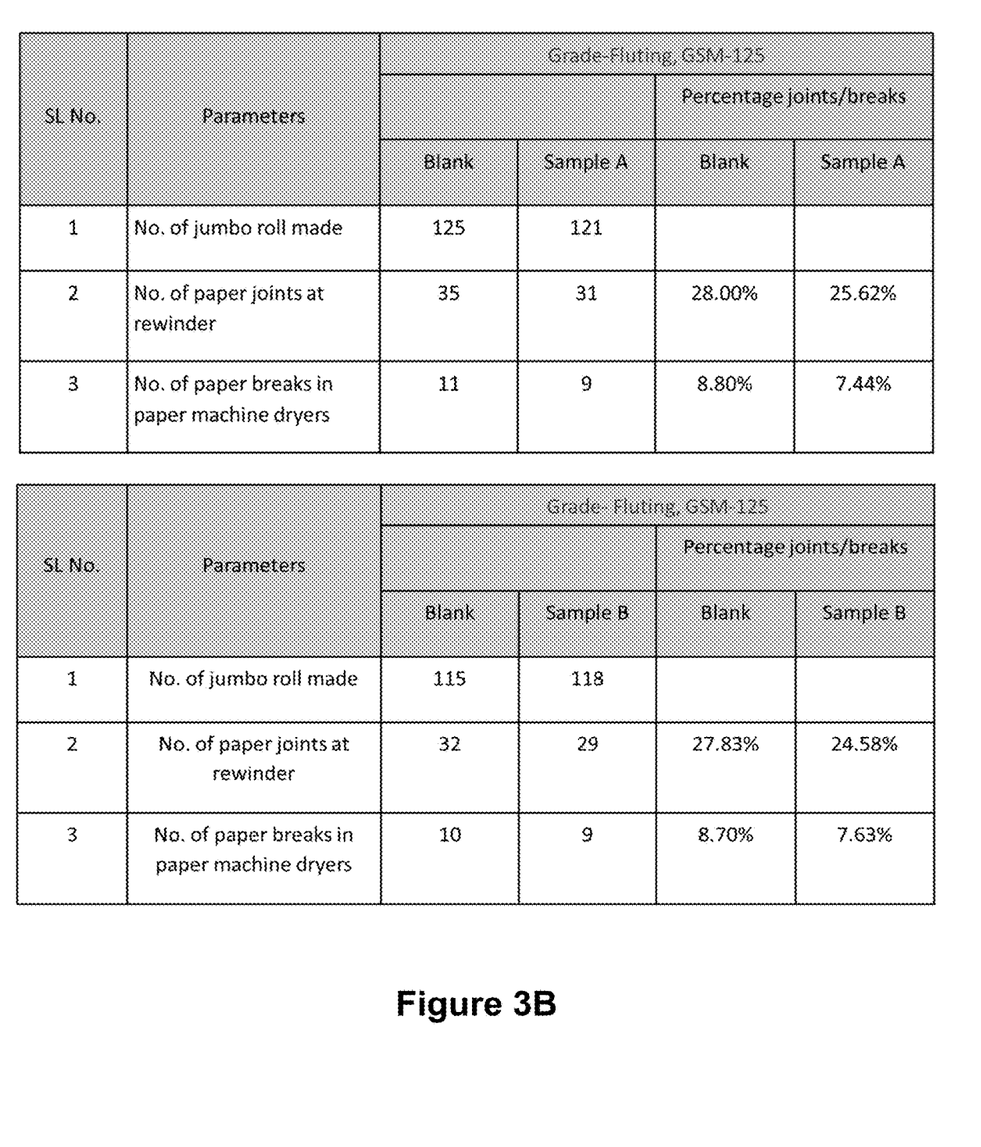
FIG. 3B shows plant trial data for Enzyme formulation "A," (top table) and Enzyme formulation "B" (bottom table), showing that Sample E (FIG. 3A) shows substantial reduction of Rewinder Breaks and Paper Breaks in machine, proving the invention.

FIG. 2A provides a table showing results of Enzyme formulation "E" on breaks occurring in paper on the paper machine dryer and rewinder, caused by stickies. Enzyme formulation "E" showed a large reduction in the number of breaks. FIG. 2B provides a table showing stickies and fluff weight collected from paper machine doctor blades using Enzyme formulation "E". Enzyme formulation "E" showed a large reduction in stickies and fluff weights collected on paper machine doctor blades. FIG. 3A shows plant trial data for Enzyme formulation "E," showing that when compared to blank, Formulation E shows fewer paper joints and paper breaks; Samples A and B (FIG. 3B), shows that these are not nearly as effective as the Sample E to show substantial reduction of Rewinder Breaks and Paper Breaks in machine. Importantly, Enzyme formulation "A," (top table) and Enzyme formulation "B" (bottom table) results show that Sample E (FIG. 3A) alone provides substantial reduction of Rewinder Breaks and Paper Breaks in machine, proving the invention.

Figure 4:
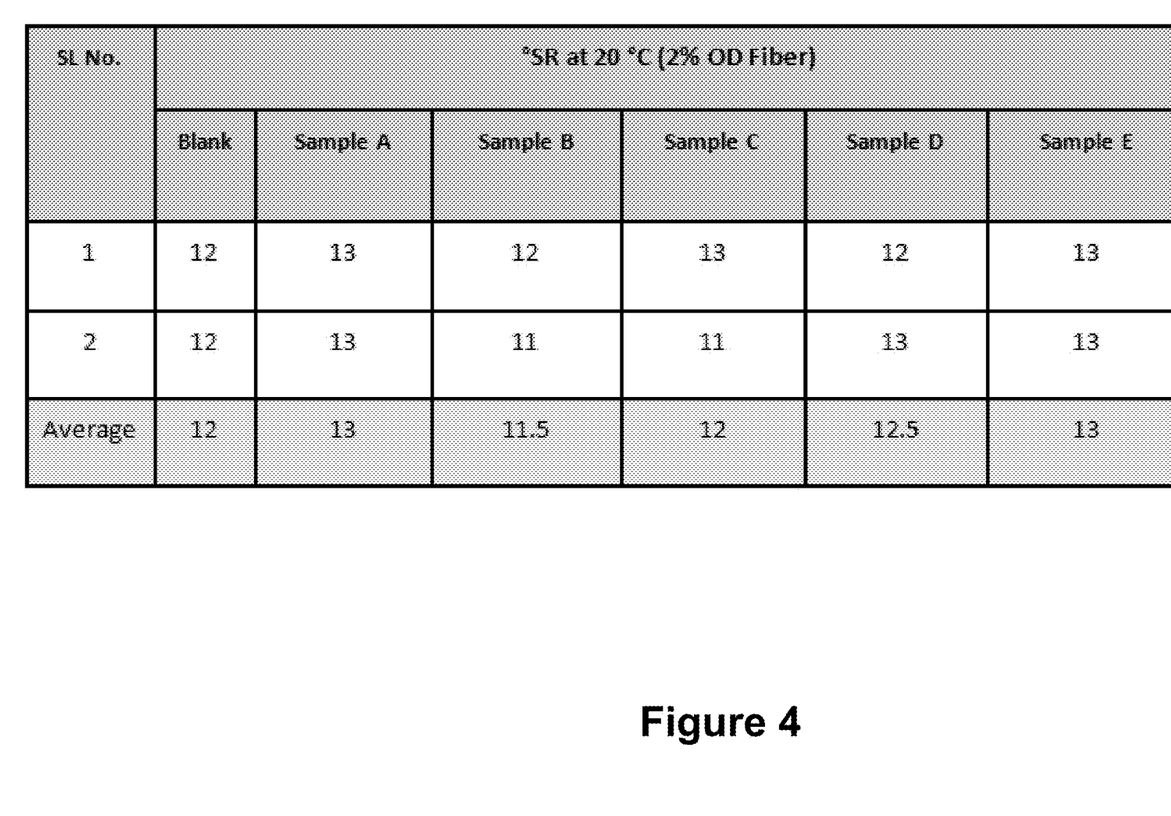
FIG. 4 shows degrees SR for pulp treated with each sample. An increase in Degree SR is interpreted as improved fiber swelling and fibrillation.
Figure 5:
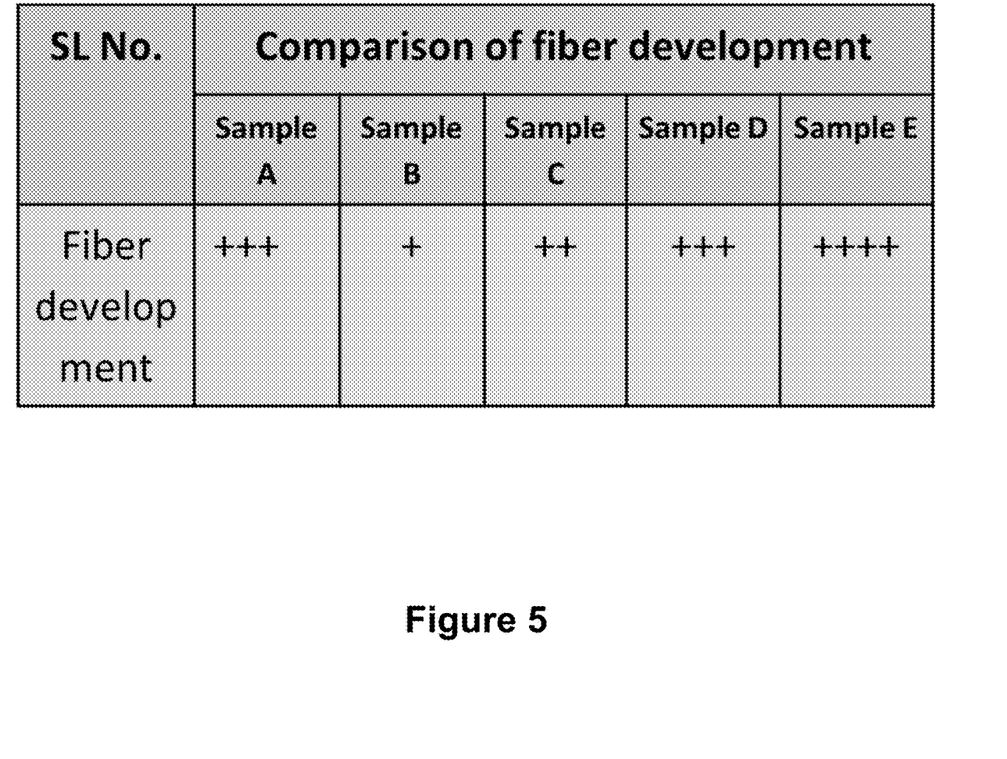
FIG. 5 shows comparative fiber development/fluff reduction for several enzyme compositions, A-E.
Figure 6:
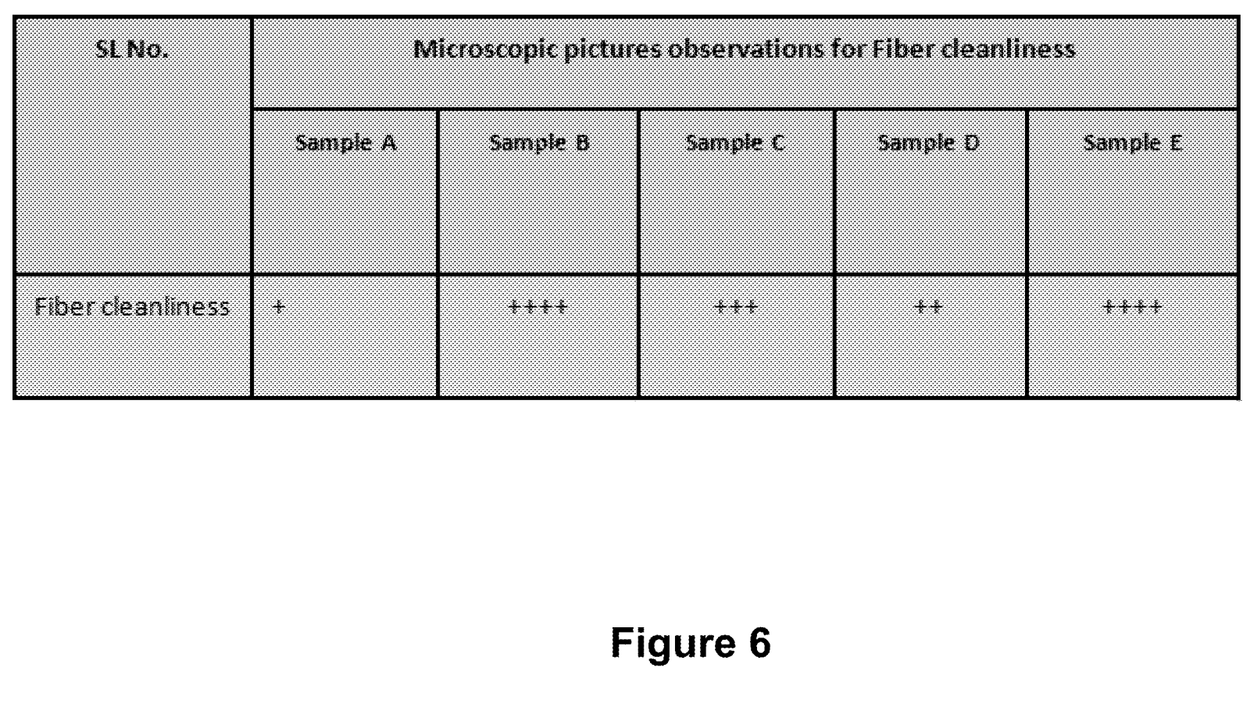
FIG. 6 shows effectiveness based on microscopic analysis for reduction in dirtiness/sticky materials.
Figure 7:
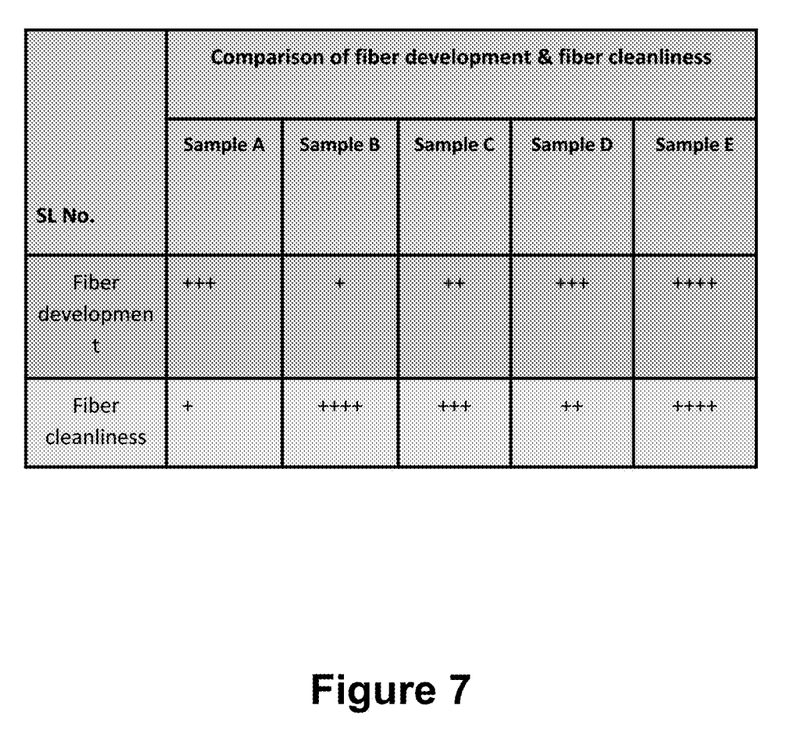
FIG. 7 shows the fiber development and cleanliness of each enzyme formulation.

FIG. 4 shows degrees SR of pulp samples treated with each sample (A-E). An increase in Degree SR is interpreted as improved fiber swelling and fibrillation. The samples show approximately the same level of degree SR. FIG. 5 shows comparative fiber development/fluff reduction for several enzyme compositions, A-E. Fiber development is best for Sample E, second best with Sample A and D, and less in Samples B and C. FIG. 6 shows effectiveness based on microscopic analysis for reduction in dirtiness/sticky materials. Again, Sample E and Sample B are the best cleanliness, Sample C and D show less cleanliness, and Sample A shows the least cleanliness. FIG. 7 shows the fiber development and cleanliness of each enzyme formulation, indicating that Sample E displays the best characteristics.

On analyzing the results of the Examples, it was observed that significant reduction of fluff generation at pre-dryer section and paper breaks due to stickies at machine and rewinder with enzyme application compared to blank, was achieved Measurement of stickies was done by using a Fine slotted screen (e.g. Pulmac Master Screen), to screen out large contaminants and then use heat and pressure to press the rejected contaminants against a surface, so that the stickies are transferred to the sheet and counted manually. (In lines of TAPPI T277 method).

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method to reduce sticky and fluff induced rewinder breaks in a paper rewinder machine by reducing the adhesive character of adhesive materials, fluff and sticky contaminants in recycled paper fibers for paper production, comprising:
   providing recycled paper fibers in aqueous solution as a pulp slurry; and
   contacting the pulp slurry with a multi-enzyme composition for a sufficient time and in a sufficient amount to reduce the adhesive character of adhesive materials, fluff and sticky contaminants, wherein the multi-enzyme composition comprises:
   21 to 24 wt % cellulase;
   21 to 24 wt % hemicellulose;
   13 to 16 wt % beta-glucosidase;
   14 to 16 wt % lipase;
   4 to 7 wt % pectate lyase;
   7 to 8 wt % esterase; and
   5 to 8 wt % laccase.

2. The method of claim 1, wherein the multi-enzyme composition is introduced during the pulping stage.

3. The method of claim 2 comprising hydrolyzing lignocellulosic components of the pulp slurry via the multi-enzyme composition thereby enhancing hydration of the recycled fiber.

4. The method of claim 1, wherein the multi-enzyme composition comprises a pectinase.

5. The method of claim 1, wherein the multi-enzyme composition is mixed with the pulp slurry in an amount of between 0 ppm and 30 ppm with the pulp slurry weight being calculated based on the dry weight of the air-dried fibers comprising the pulp slurry.

6. The method of claim 1, wherein the multi-enzyme composition is added after a step of hot dispersion in the stock preparation process.

7. The method of claim 1, wherein the multi-enzyme composition is mixed with the pulp slurry in an amount of between 0 ppm and 30 ppm with the pulp slurry weight being calculated based on dry weight of the air-dried fibers present in the pulp slurry.

8. A method of making paper or paperboard products comprising:
   forming a pulp slurry comprising fibers obtained from recycled paper or paperboard;
   treating said slurry with a composition comprising a multi-enzyme composition for a sufficient time and in a sufficient amount to control organic contaminants present in the fiber, wherein the multi-enzyme composition comprises:
   21 to 24 wt % cellulase;
   21 to 24 wt % hemicellulose;
   13 to 16 wt % beta-glucosidase;
   14 to 16 wt % lipase;
   4 to 7 wt % pectate lyase;
   7 to 8 wt % esterase;
   5 to 8 wt % laccase; and
   forming the treated slurry into paper or paperboard products.

9. The method of claim 8, wherein the multi-enzyme composition comprises a pectinase.

10. The method of claim 8 comprising hydrolyzing lignocellulosic components of the pulp slurry via the multi-enzyme composition thereby enhancing hydration of the recycled fiber.

* * * * *